United States Patent [19]
Ray et al.

[11] Patent Number: 4,570,380
[45] Date of Patent: Feb. 18, 1986

[54] ROUTE TO HYBRID COTTON PRODUCTION

[75] Inventors: Levon L. Ray, Lubbock; Jose L. Longoria, Plainview, both of Tex.

[73] Assignee: Ciba-Geigy Corporation, Ardsley, N.Y.

[21] Appl. No.: 675,751

[22] Filed: Nov. 28, 1984

[51] Int. Cl.$^4$ .............................................. A01H 1/02
[52] U.S. Cl. .................................... 47/58; 47/DIG. 1
[58] Field of Search ............................ 47/58, DIG. 1

[56] References Cited

PUBLICATIONS

William R. Meredith, Jr., "Influence of Leaf Morphology on Lint Yield of Cotton-Enhancement by the Sub Okra Trait," Crop Science, vol. 24, pp. 855 to 857, Sep.-Oct. 1984.
Canadian Pat. No. 668,452, "Production of Hybrid Cottonseed," Frank M. Eaton, Aug. 13, 1963.
Vesta G. Meyer, "Male Sterility from *Gossypium harknessii*," J. of Heredity, vol. 66, pp. 23 to 27 (1975).
Joseph O. Moffett, Lee S. Stith, and Charles W. Shipman, "Producing Hybrid Cotton Seed on the High Plains of Texas," Beltwide Cotton Production Research Conference Proceedings, Atlanta, GA, pp. 90 to 92 (1977).
J. B. Weaver, Jr., "Present Status of Fertility Restoration in Cytoplasmic Male-Sterile Upland Cotton," Beltwide Cotton Production Research Conferences Proceedings, Atlanta, GA, pp. 95 to 96 (1977).
Joseph O. Moffett, Lee S. Stith, and Charles W. Shipman, "Producing Hybrid Cotton Seed on a Field Scale by Using Honey Bees as Pollinators," Beltwide Cotton Production Research Conferences Proceedings, Dallas TX, pp. 77 to 79 (1978).
W. R. Meredith, Jr., Vesta Meyer, B. W. Hanny, and J. C. Bailey, "Influence of Five Gossypium Species Cytoplasms on Yield, Yield Components, Fiber Properties, and Insect Resistance in Upland Cotton," Crop Science, vol. 19, pp. 647 to 650, Sep.-Oct., 1979.
Richard H. Sheetz and James B. Weaver, Jr., "Pima Fertility Enhancer Factor: Inheritance and Use in Hybrid Cotton Production," Beltwide Cotton Production Research Conferences Proceedings, St. Louis, MO, p. 82 (1980).
R. H. Sheetz and J. B. Weaver, Jr., "Inheritance of a Fertility Enhancer Factor from Pima Cotton when Transferred into Upland Cotton with *Gossypium harknessii* Brandegee Cytoplasm," Crop Science, vol. 20, pp. 272 to 275, Mar.-Apr., 1980.

(List continued on next page.)

Primary Examiner—Robert E. Bagwill
Attorney, Agent, or Firm—Burns, Doane, Swecker & Mathis

[57] ABSTRACT

An improved procedure utilizing a cytoplasmic-genetic male sterile system for forming $F_1$ hybrid cottonseeds (i.e., seeds capable of forming hybrid cotton plants of the first filial generation) is provided which is readily amenable to the determination and maintenance of the desired level of purity in the hybrid cottonseed product. The parent plants required for hybrid formation are each homozygotes (as described) with respect to differing leaf shape configurations (i.e., the male sterile female parent plants have a broad-leafed configuration and the fertility-restoring male parent has a narrow-leafed configuration). The resulting $F_1$ hybrid cotton plants are heterozygotes with respect to leaf shape phenotype and can be visually differentiated from each parent. Following the $F_1$ hybrid-forming cross-pollination, at least a portion of the resulting cottonseeds are grown, and the approximate proportion of $F_1$ hybrid cottonseeds present in the cottonseed product is determined on the basis of the respective leaf shapes which are exhibited. The plurality of the hybrid-forming parental lines additionally can be enhanced with ease through an observation of the respective leaf shape configuration followed by the timely removal of contaminant cotton plants which lack the requisite leaf configuration. The process of the present invention accordingly provides an efficient route to overcome quality control difficulties heretofore associated with hybrid cotton production in the prior art.

28 Claims, 3 Drawing Figures

OTHER PUBLICATIONS

Delbert C. Hess, "Hybrid Cotton Development," Beltwide Cotton Mechanization-Production Research Conference Proceedings, New Orleans, LA, pp. 28 to 29 (1981).

J. E. Quisenberry and R. E. Dilbeck, "Stormproof Boll in Upland Cotton III. Genotype-Environment Interaction and Genetic Analysis," Crop Science, vol. 21, pp. 511 to 514, Jul.-Aug., 1981.

James B. Weaver, Jr., "Recent Significant Observations on the Development of Hybrid Cotton," Beltwide Cotton Production Research Conferences Proceedings, Las Vegas, NV, pp. 88 to 90 (1982).

James B. Weaver, Jr., "Interspecific Hybrid Cotton as a Trap Crop for Boll Weevil Control," Beltwide Cotton Production Research Conferences Proceedings, Las Vegas, NV, pp. 207 to 209 (1982).

Frank L. Carter, Dick D. Davis and Elbert R. Jaycox, "Effect of Planting Pattern on Cross Pollination in Hybrid NX-1 Seed Production," Beltwide Cotton Production Conferences Proceedings, Atlanta, GA, pp. 130 to 131 (1984).

J. B. Weaver, "Hybrid Cotton Sets a Good Weevil Trap," Progressive Farmer, Aug., 1984.

J. A. Andries, J. E. Jones, L. W. Sloane, and J. G. Marshall, "Effects of Okra Leaf Shap on Boll Rot, Yield and Other Important Characters of Upland Cotton, *Gossypium hirsutum* L.," Crop Science, vol. 9, pp. 705 to 710, Nov.-Dec., 1969.

J. A. Andries, J. E. Jones, L. W. Sloane, and J. G. Marshall, "Effects of Supra Okra Leaf Shap on Boll Rot, Yield, and Other Characters of Upland Cotton, *Gossypium hirsutum* L.," Crop Science, vol. 10, pp. 403 to 407, Jul.-Aug., 1970.

J. E. Jones, "Effect of Morphological Characters of Cotton on Insects and Pathogens," Beltwide Cotton Production Research Conferences Proceedings, Las Vegas, NV, pp. 88 to 92 (1972).

J. E. Jones, W. D. Caldwell, M. R. Milam, and D. F. Clower, "Gumbo and Pronto: Two New Open-Canopy Varieties of Cotton," Circular No. 103, Louisiana State University, Dec., 1976.

W. D. Caldwell, D. R. Melville, A. M. Pavloff, and J. E. Jones, "Agronomic Studies of Okra and Supra Okra Leaf Cotton," Beltwide Cotton Production Research Conferences Proceedings, Las Vegas, NV, pp. 83 to 84 (1977).

L. S. Bird, F. M. Bourland, R. G. Percy, J. E. Hood, and D. L. Bush, "Additional Progress in Developing Okra Leaf, Frego Bract and Glabrous Multi-Adversity Resistant Cottons," Beltwide Cotton Production Research Conferences Proceedings, Atlanta, GA, pp. 107 to 109 (1977).

J. B. Weaver, Jr., "Observations on Bee Activity in Several Genotypes of Cotton," Beltwide Cotton Production Research Conferences Proceedings, Dallas, TX, pp. 76 to 77 (1978).

Jack E. Jones, D. T. Bowman, J. W. Brand, W. D. Caldwell, and D. F. Clower, "Genetic Improvement of Open-Canopy Cottons," Beltwide Cotton Production Research Conferences Proceedings, St. Louis, MO, pp. 72 to 74 (1980).

F. Karami, D. R. Krieg, and J. E. Quisenberry, "Water Relations and Carbon-14 Assimilation of Cotton with Different Leaf Morphology," Crop Science, vol. 20, pp. 421 to 426, Jul.-Aug., 1980.

Jack E. Jones, "The Present State of the Art and Science of Cotton Breeding for Leaf-Morphological Types," Beltwide Cotton Production Research Conferences Proceedings, Las Vegas, NV, pp. 93 to 99 (1982).

J. W. Weaver, Jr. and Ralph Graham, "Behavior of Boll Weevils on Cytoplasmic Male-Sterile Cotton in Isolated Plots," Beltwide Cotton Production Research Conferences Proceedings, Atlanta, GA, pp. 100 to 102 (1977).

K. N. Gururajan and K. Srinivasan, "Note on the Use of Okra-Leaf Male-Sterile Line in the Production of Hybrid Cotton," Indian J. Agric. Sci., vol. 52(1), pp. 20 to 21, Jan., 1982.

ROUTE TO HYBRID COTTON PRODUCTION

BACKGROUND OF THE INVENTION

It is well known that when different plant lines are cross-pollinated, one can achieve in the offspring a highly desirable heterosis or hybrid vigor which advantageously provides increased yields of the desired crop.

Representative crops which have been successfully hybridized in the past include sugar beets, corn (See, U.S. Pat. No. 3,753,663 to Jones), sorghum, alfalfa (See, U.S. Pat. No. 3,570,181 to Davis), wheat, sunflowers, cotton, rice (See, U.S. Pat. No. 4,305,225 to Yuan), cucumbers, onions, carrots, and tomatoes.

It is well-recognized that cotton (plants of genus Gossypium) is an important crop which is grown in many parts of the world. While the necessary plants for hybrid cottonseed production are known and available, only limited hybrid cotton production has been carried out to date. For instance, in some parts of the world cotton plants have been emasculated by hand and the pollen has been transferred to the female parent by hand.

While the necessary cotton plants for a cytoplasmic-genetic male sterile system for hybrid cottonseed production are known and available, such system has heretofore been largely impossible to reliably implement on a commercial basis since it has proven to be a tremendous undertaking to monitor the level of hybridization in the final cottonseed product and to determine and maintain purity in the parental lines.

Heretofore, most commercially grown cotton varieties have been the broad-leafed varieties. However, it has been recognized that under some growing conditions the narrow-leafed cotton varieties (e.g., Pronto and Gumbo) may perform better. For instance, when the growing conditions are highly conducive to cotton boll rot, then the more open canopy growth habit of the cotton plants made possible with the narrow-leafed cotton varieties may be preferable. Such openness will better enable sunlight to reach the cotton bolls and for the plant to better receive an insecticide at its innermost locations. Also, studies have been conducted in the past with respect to insect visitation preferences concerning broad- and narrow-leafed cotton varieties. For a recent discussion of the effects of cotton leaf shape on yield see "Influence of Leaf Morphology on Lint Yield of Cotton-Enhancement by the Sub Okra Trait," William R. Meredith Jr., *Crop Science*, Vol. 24, p. 855 to 857, Sept.-Oct. 1984.

Representative prior publications which concern the formation of hybrid cottonseeds are the following:

(1) Canadian Pat. No. 668,452, "Production of Hybrid Cottonseed," Frank M. Eaton, Aug. 13, 1963.

(2) Vesta G. Meyer, "Male Sterility From *Gossypium harknessii*," *J. of Heredity*, Vol. 66, p. 23 to 27 (1975).

(3) Joseph O. Moffett, Lee S. Stith, and Charles W. Shipman, "Producing Hybrid Cotton Seed on the High Plains of Texas," Beltwide Cotton Production Research Conferences Proceedings, Atlanta, Ga., p. 90 to 92 (1977).

(4) J. B. Weaver, Jr., "Present Status of Fertility Restoration in Cytoplasmic Male-Sterile Upland Cotton," Beltwide Cotton Production Research Conferences Proceedings, Atlanta, Ga., p. 95 to 96 (1977).

(5) Joseph O. Moffett, Lee S. Stith, and Charles W. Shipman, "Producing Hybrid Cotton Seed on a Field Scale by Using Honey Bees as Pollinators," Beltwide Cotton Production Research Conferences Proceedings, Dallas, Tex., p. 77 to 79 (1978).

(6) W. R. Meredith, Jr., Vesta Meyer, B. W. Hanny, and J. C. Bailey, "Influence of Five Gossypium Species Cytoplasms on Yield, Yield Components, Fiber Properties, and Insect Resistance in Upland Cotton," *Crop Science*, Vol. 19, p. 647 to 650, Sept.-Oct. 1979.

(7) Richard H. Sheetz and James B. Weaver, Jr., "Pima Fertility Enhancer Factor: Inheritance and Use in Hybrid Cotton Production," Beltwide Cotton Production Research Conferences Proceedings, St. Louis, Mo., p. 82 (1980).

(8) R. H. Sheetz and J. B. Weaver, Jr., "Inheritance of a Fertility Enhancer Factor From Pima Cotton When Transferred Into Upland Cotton With *Gossypium harknessii* Brandegee Cytoplasm," *Crop Science*, Vol. 20, p. 272 to 275, Mar.-April 1980.

(9) Delbert C. Hess, "Hybrid Cotton Development," Beltwide Cotton Mechanization-Production Research Conferences Proceedings, New Orleans, La., p. 28 to 29 (1981).

(10) J. E. Quisenberry and R. E. Dilbeck, "Stormproof Boll in Upland Cotton III. Genotype-Environment Interaction and Genetic Analysis," *Crop Science*, Vol. 21, p. 511 to 514, July-August 1981.

(11) James B. Weaver, Jr., "Recent Significant Observations on the Development of Hybrid Cotton," Beltwide Cotton Production Research Conferences Proceedings, Las Vegas, Nev., p. 88 to 90 (1982).

(12) James B. Weaver, Jr., "Interspecific Hybrid Cotton as a Trap Crop for Boll Weevil Control," Beltwide Cotton Production Research Conferences Proceedings, Las Vegas, Nev., p. 207 to 209 (1982).

(13) Frank L. Carter, Dick D. Davis and Elbert R. Jaycox, "Effect of Planting Pattern on Cross Pollination in Hybrid NX-1 Seed Production," Beltwide Cotton Production Conferences Proceedings, Atlanta Ga., p. 130 to 131 (1984).

(14) J. B. Weaver, "Hybrid Cotton Sets a Good Weevil Trap," Progressive Farmer, August 1984.

Representative prior publications which concern to at least some degree leaf shape configurations in cotton plants are the following:

(1) J. A. Andries, J. E. Jones, L. W. Sloane, and J. G. Marshall, "Effects of Okra Leaf Shape on Boll Rot, Yield and Other Important Characters of Upland Cotton, *Gossypium hirsutum* L., " *Crop Science*, Vol. 9, p. 705 to 710, Nov.-Dec. 1969.

(2) J. A. Andries, J. E. Jones, L. W. Sloane, and J. G. Marshall, "Effects of Supra Okra Leaf Shape on Boll Rot, Yield, and Other Characters of Upland Cotton, *Gossypium hirsutum* L.," *Crop Science*, Vol. 10, p. 403 to 407, July-Aug. 1970.

(3) J. E. Jones, "Effect of Morphological Characters of Cotton on Insects and Pathogens," Beltwide Cotton Production Research Conferences Proceedings, Las Vegas, Nev., p. 88 to 92 (1972).

(4) J. E. Jones, W. D. Caldwell, M. R. Milam, and D. F. Clower, "Gumbo and Pronto: Two New Open-Canopy Varieties of Cotton," Circular No. 103, Louisiana State University, December 1976.

(5) W. D. Caldwell, D. R. Melville, A. M. Pavloff, and J. E. Jones, "Agronomic Studies of Okra and Super Okra Leaf Cotton," Beltwide Cotton Production Research Conferences Proceedings, Las Vegas, Nev., p. 83 to 84 (1977).

(6) L. S. Bird, F. M. Bourland, R. G. Percy, J. E. Hood, and D. L. Bush, "Additional Progress in Developing Okra Leaf, Frego Bract and Glabrous Multi-Adversity Resistant Cottons," Beltwide Cotton Production Research Conferences Proceedings, Atlanta, Ga., p. 107 to 109 (1977).

(7) J. B. Weaver, Jr., "Observations on Bee Activity in Several Genotypes of Cotton," Beltwide Cotton Production Research Conferences Proceedings, Dallas, Tex., p. 76 to 77 (1978).

(8) Jack E. Jones, D. T. Bowman, J. W. Brand, W. D. Caldwell, and D. F. Clower, "Genetic Improvement of Open-Canopy Cottons," Beltwide Cotton Production Research Conferences Proceedings, St. Louis, Mo., p. 72 to 74 (1980).

(9) F. Karami, D. R. Krieg, and J. E. Quisenberry, "Water Relations and Carbon-14 Assimilation of Cotton With Different Leaf Morphology," Crop Science, Vol. 20, p. 421 to 426, July–Aug. 1980.

(10) Jack E. Jones, "The Present State of the Art and Science of Cotton Breeding for Leaf-Morphological Types," Beltwide Cotton Production Research Conferences Proceedings, Las Vegas, Nev., p. 93 to 99 (1982).

The following articles mention the use of narrow leafshaped cotton plants during the production of hybrid cotton:

(1) J. B. Weaver, Jr., and Ralph Graham, "Behavior of Boll Weevils on Cytoplasmic Male-Sterile Cotton in Isolated Plots," Beltwide Cotton Production Research Conferences Proceedings, Atlanta, Ga., p. 100 to 102 (1977).

(2) K. N. Gururajan and K. Srinivasan, "Note on the Use of Okra-Leaf Male-Sterile Line in the Production of Hybrid Cotton," Indian J. Agric. Sci., Vol. 52(1), p. 20 to 21, January 1982.

In Article (1) the use of cytoplasmic male sterile cotton plants having a narrow leaf configuration as a trap crop for insects is mentioned. In Article (2) the possible worth of the okra leaf character with respect to cotton yield is discussed. Each of the articles is silent with respect to an overall commercially practicable process wherein the purity of the hybrid cottonseed product is determined and/or controlled during its production by any means.

It is an object of the present invention to provide an improved process for forming $F_1$ hybrid cottonseeds which is capable of being readily implemented on a commercial scale.

It is an object of the present invention to provide an improved process for forming $F_1$ hybrid cottonseeds on an efficient basis wherein the degree of purity of the product readily can be determined on a reliable basis.

It is an object of the present invention to provide an improved process for forming $F_1$ hybrid cottonseeds on an efficient basis wherein the parent plants optionally can be grown in bulk in the same area and the degree of hybrid purity in the product readily can be determined on a reliable basis.

It is an object of the present invention to provide an improved process for forming $F_1$ hybrid cottonseeds on an efficient basis wherein sources of non-hybrid contamination in the product readily can be identified as to their likely source.

It is an object of the present invention to provide an improved process for forming $F_1$ hybrid cottonseeds on an efficient basis wherein in a preferred embodiment contamination in the parental lines readily is identified and is eliminated so as to enhance their purity and the purity of the $F_1$ hybrid cottonseed product.

It is an object of the present invention to provide an improved process utilizing a cytoplasmic-genetic male sterile system for the production of $F_1$ hybrid cottonseeds wherein a marker system is utilized for purity control which is readily identifiable, is highly reliable, and is not influenced by the environment.

It is another object of the present invention to provide an improved process for forming $F_1$ hybrid cottonseeds wherein the required cross-pollination readily can be carried out with the aid of pollen-carrying insects.

It is another object of the present invention to provide an improved process for forming $F_1$ hybrid cottonseeds wherein an abundant and consistent supply of pollen is provided by the male parent plants.

It is yet another object of the present invention to provide an improved process for forming $F_1$ hybrid cottonseeds wherein pollen-carrying insects are provided good accessibility to amply exposed flowers of the male parent plants.

It is a further object of the present invention to provide an improved process for forming $F_1$ hybrid cottonseeds wherein the respective parent plants and the resulting $F_1$ hybrid plants can be readily identified visually thereby facilitating a more positive identification of field plots.

These and other objects, as well as the scope, nature, and utilization of the claimed process, will be apparent to those skilled in the art from the following detailed description and appended claims.

SUMMARY OF THE INVENTION

It has been found that an improved process for the efficient production of seeds capable of growing $F_1$ hybrid cotton plants comprises:

(a) growing in a planting area a substantially random population of (i) broad-leafed male sterile cotton plants wherein the broad leaf configuration is attributable to a recessive gene pair for such characteristic and the male sterility is attributable to the combination of an atypical Cms cytoplasm and a recessive genetic system for male sterility, and (ii) narrow-leafed male fertile cotton plants wherein the narrow leaf configuration is attributable to a partially dominant gene pair for such characteristic and the male fertility is attributable to a dominant genetic system for fertility restoration;

(b) pollinating the substantially random population of cotton plants whereby cottonseeds are formed on the male sterile cotton plants (i) which are capable of growing male fertile $F_1$ hybrid cotton plants which possess a visually observable heterozygous leaf configuration that is intermediate in configuration between the leaf configurations of parent plants (i) and (ii), and cottonseeds are formed on the narrow-leafed male fertile cotton plants (ii) which are capable of growing narrow-leafed non-hybrid cotton plants;

(c) recovering cottonseeds which have formed on the substantially random population of cotton plants in the planting area;

(d) growing at least a portion of the cottonseeds recovered in step (c); and (e) determining the approximate proportion of $F_1$ hybrid cottonseeds present in the cottonseeds recovered in step (c) on the basis of the respective leaf shapes of the plants grown in step (d).

It further has been found that an improved process for the efficient production of seeds capable of growing $F_1$ hybrid cotton plants comprises:

(a) growing a substantially uniform first population of broad-leafed male sterile cotton plants wherein the broad leaf configuration is attributable to a recessive gene pair for such characteristic and the male sterility is attributable to a combination of an atypical Cms cytoplasm and a recessive genetic system for male sterility in pollinating proximity to a substantially uniform second population of narrow-leafed male fertile cotton plants wherein the narrow leaf configuration is attributable to a partially dominant gene pair for such characteristic and the male fertility is attributable to a dominant genetic system for fertility restoration;

(b) pollinating the broad-leafed male sterile cotton plants of the first population with pollen from the narrow-leafed male fertile cotton plants of the second population whereby cottonseeds are formed on the broad-leafed male sterile cotton plants of the first population which are capable of growing male fertile $F_1$ hybrid cotton plants which possess a visually observable heterozygous leaf configuration that is intermediate in configuration between the leaf configurations of the bulk of the plants of the first and second populations;

(c) recovering the cottonseeds which have formed on the plants of the first population;

(d) growing at least a portion of the cottonseeds recovered in step (c); and (e) determining the approximate proportion of $F_1$ hybrid cottonseeds present in the cottonseeds recovered in said step (c) on the basis of the respective leaf shapes of the plants grown in step (d).

It should be understood that the specific number of lobes present on a given cotton plant leaf may vary as described herein and is possibly influenced by genetic factors, the location of the leaf on the cotton plant, and the environment.

DESCRIPTION OF PREFERRED EMBODIMENTS

The cytoplasmic-genetic system for hybrid cotton production utilized in the process of the present invention is known and has previously been reported in the literature by researchers such as Vesta G. Meyer and James B. Weaver, Jr. The present invention provides for the first time a reliable procedure for the efficient determination and maintenance of the desired level of purity in the hybrid cottonseed product.

Figure 1:
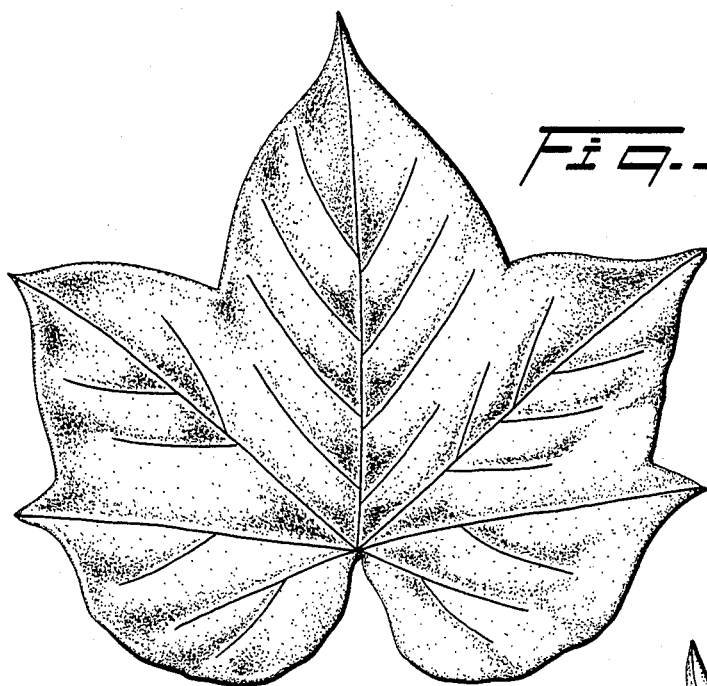
FIG. 1 shows a representative leaf configuration for a broad-leafed female fertile male sterile cotton plant which is suitable for use in the improved process of the present invention.

In accordance with the concept of the present invention male sterile female, fertile cotton plants are selected for use as the seed parents which additionally have the usual broad leaf configuration. Such broad leaf configuration is attributable to a recessive gene pair for such characteristic (e.g., gene pair 11). FIG. 1 illustrates a typical cotton leaf having such broad leaf configuration. As will be apparent to those skilled in cotton plant leaf morphology, not all leaves on a given cotton plant will likely possess five lobes as illustrated. For instance, cotton plant leaves having from 1 to 5 lobes commonly will be encountered with 3 to 5 lobes per leaf being the more frequent. It further will be apparent to those skilled in cotton plant leaf morphology that the first leaves formed on a given cotton plant will tend to have a lesser number of lobes. Regardless of the number of lobes present, the cotton plant leaf lobes of the female parent will be substantially wider than those of the male parent discussed hereafter and readily distinguished in the adult plant. Also, the degree of cleavage or division between adjoining leaf lobes of the female parent will be substantially less.

Broad-leafed female parents are selected for use in the process of the present invention in which the male sterility is attributable to an atypical Cms (i.e., cytoplasmic male sterile) cytoplasm and a recessive genetic system for male sterility. In such recessive genetic system the appropriate genes are present in combination with the Cms cytoplasm for the male sterility characteristic to be expressed on a reliable basis. The male sterile cotton plants utilized by necessity possess at least one pair of recessive genes (e.g., rfrf) which are incapable of restoring male fertility. Additionally, such male sterile female parent plants may possess either the dominant gene pair (e.g., EE) or the recessive gene pair (e.g., ee) for enhancing fertility restoration. However, if the narrow-leafed male parent plants (described hereafter) lack the dominant gene pair for enhancing fertility restoration EE, it is recommended that these genes be present in the broad-leafed male sterile plants. Good results have been achieved when the male sterile female parents possess the Cms cytoplasm in combination with the recessive rfrf and ee gene pairs. Since the required Cms cytoplasm is not transmitted through the pollen, it can be considered cytoplasmic, non-Mendelian, extrachromosomal, uniparental, and maternal.

The male sterile cotton plants utilized in the process of the present invention are fully female fertile but produce no viable pollen, thereby precluding the possibility of unwanted self-pollination. These plants accordingly can satisfactorily serve as the female or seed parents while using the hybridization procedures described hereafter. Accordingly, all seeds formed on the male sterile cotton plants following pollination by the male parent will be capable of forming the desired $F_1$ hybrid cotton plants having a distinctive heterozygous leaf configuration (described hereafter).

Cytoplasmically male sterile cotton plants having the requisite genetic makeup in combination with the broad leaf configuration previously have been reported and presently are available from many public and private cotton breeding programs. Such plants commonly possess a *Gossypium harknessii* Brandg. cytoplasm in combination with the requisite genes for broad leaf configuration and male sterility. Respresentative sources for seeds capable of forming the cytoplasmically male sterile cotton plants are Texas A & M University (College Station, Texas), Mississippi State University (State College, Mississippi), New Mexico State University (University Park, New Mexico), University of Georgia (Athens, Georgia), etc. Good results have been obtained when using Tamcot A-788 as the cytoplasmically male sterile cotton plants. Such Tamcot A-788 cytoplasmic male sterile line was developed in the Texas A & M University system and has been available since 1979 from the Texas Agricultural Experiment Station, Route No. 3, Lubbock, Texas 79401. Also, seeds derived from Tamcot A-788 through selection have been designated No. RA-A30 and have been deposited in the National Seed Storage Laboratory at Fort Collins, Colo., under Laboratory Accession No. GH-2375 Ser. No. 190,936.

The requisite cytoplasmic and genetic makeup for the broad-leafed male sterile female parent can be readily transferred to other existing varieties or lines (e.g., those of the *Gossypium hirsutum* L. genotype) by the backcross technique using the previously available male sterile cotton plants as the female parents and the variety or line of *Gossypium hirsutum* as the recurring male parent for a number of generations (e.g., four or five generations). The offspring will be female fertile and cytoplasmic male sterile, and the male sterile and maintainer lines will then be substantially identical in their genetic complement.

Once the broad-leafed male sterile plants for use in the process of the present invention are selected, they may be maintained and multiplied by crossing with suitable maintainer plants which lack the atypical Cms cytoplasm but otherwise include a recessive genetic system for male sterility (e.g., rfrf and ee gene pairs or rfrf and EE gene pairs) and the recessive genes for a broad leaf configuration. Such maintainer plants will possess a cytoplasm of the normal type (i.e., an N cytoplasm). It has been found that cotton plants of *Gossypium hirsutum* genotype can be used to develop suitable maintainer lines. Representative sources for seeds capable of forming satisfactory maintainer cotton plants for specific cytoplasmically male sterile cotton plants are Texas A & M University, Mississippi State University, New Mexico State University, University of Georgia, etc. A good maintainer for the cytoplasmically male sterile Tamcot A-788 cotton plants is the Tamcot 788 line. The Tamcot 788 line was developed in the Texas A & M University system and is available from the Texas Agricultural Experiment Station, Route No. 3, Lubbock, Tex. 79401. The Tamcot A-788 cytoplasmically male sterile line was developed from this Tamcot 788 line. Seeds derived from the Tamcot 788 line through selection have been designated No. RA-B30 and have been deposited in the National Seed Storage Laboratory at Fort Collins, Colo., under Laboratory Accession No. GH-2376 Ser. No. 190,937.

Also, commercially available varieties or lines of *Gossypium hirsutum* may be used as suitable maintainer lines provided they carry the requisite genes for a broad leaf configuration and possess a substantially identical genetic complement to that of the cytoplasmically male sterile cotton plants. As will be apparent to those skilled in plant breeding, the specific cytoplasmically male sterile and maintainer plants selected will be influenced by the growing area in which the $F_1$ hybrid plants are ultimately to be grown. For instance, under appropriate circumstances varieties such as Stoneville 825, Paymaster 404, Acala 1517-70, Deltapine 61, DES 024, Tamcot SP37H, etc., may be used as maintainer plants provided one first has developed the required cytoplasmically male sterile plants having a substantially identical genetic complement by the backcross technique as previously described. Also, as will be apparent to those skilled in plant technology, the choice will often be influenced by the combining ability with the fertility restoring male parent (discussed hereafter) which is chosen for the production of the $F_1$ hybrid in accordance with the process of the present invention.

Figure 2:
FIG. 2 shows a representative leaf configuration for a narrow-leafed (i.e., okra-leafed) male fertile cotton plant which is suitable for use in the improved process of the present invention.

In accordance with the concept of the present invention, male fertile cotton plants are selected for use as the male parents which additionally have the less frequently encountered narrow-leafed configuration. Such narrow leaf configuration is attributable to a partially dominant gene pair (e.g., LL) for such characteristic. Such dominance by necessity is incomplete, in the sense that when crossed with the female parents, an $F_1$ hybrid is produced having a heterozygous leaf configuration that is intermediate in configuration between the leaf configurations of the parent plants (as described hereafter). FIG. 2 illustrates a typical cotton leaf having a narrow leaf configuration (i.e., an okra leaf configuration). As will be apparent to those skilled in cotton plant leaf morphology, not all leaves present on a given cotton plant are likely to possess the exact number of lobes illustrated in FIG. 2. Regardless of the number of lobes present, the leaf lobes of the male parent will be substantially narrower than those of the female parent previously discussed and readily distinguished in the adult plant. Also, there will be readily observable deeper cleavage or division between the adjoining cotton plant leaf lobes of the male parent. In addition to the okra leaf configuration illustrated in FIG. 2, other narrow-leafed configurations attributable to a dominant gene pair, such as sub-okra, super-okra, laciniate, etc., may be selected. Such various narrow-leafed configurations may be attributable to the following gene pairs as reported in the literature:

| Narrow Leaf Configuration | Partially Dominant Gene Pairs |
| --- | --- |
| okra | $L^oL^o$ |
| sub-okra | $L^uL^u$ |
| super-okra | $L^sL^s$ |
| laciniate | $L^lL^l$ |

The preferred leaf configuration for the narrow-leafed male fertile cotton plants is okra-leaf substantially as illustrated in FIG. 2.

The narrow-leafed male fertile cotton plants which are employed in the process of the present invention are fully male fertile (i.e., they produce an ample quantity of viable pollen to accomplish the desired cross-pollination) and are capable through a dominant genetic system of restoring fertility in the $F_1$ hybrid when crossed with the aforementioned male sterile plants. For instance, such narrow-leafed male fertile plants must possess a pair of dominant fertility restoring genes (e.g., RfRf). Additionally, if the broad-leafed male sterile female parent lacks the dominant gene pair for enhancing fertility restoration (e.g., EE), then it is recommended that such genes be provided in the male parent in the dominant form, and not in the recessive form (e.g., ee). The cytoplasm of the narrow-leafed male fertile cotton plants may be either cytoplasmic or normal, and preferably is cytoplasmic since plants with weak fertility genes can be more readily identified and removed. The flowers containing viable pollen preferably are produced in abundance as is a characteristic of many narrow-leafed cotton varieties. It also is preferable to select as male parents those cotton plant varieties which flower as soon as or before the female parents. Accordingly, pollen is present when the first blossoms appear on the male sterile female parents and the blossoming times are well synchronized. Such synchronization can be enhanced by planting the two diverse parents at different times taking into consideration their respective ages when blossoming commonly occurs.

The narrow-leafed male fertile cotton plants which are employed in the process of the present invention may be obtained from existing cotton germ plasms by conventional selection and breeding techniques. For instance, Dr. James B. Weaver, Jr., of the University of Georgia (Athens, Ga.) has discussed in the technical literature and is making available to plant researchers a number of cotton stocks which possess the requisite dominant genetic system for fertility restoration when crossed with cytoplasmically male sterile cotton plants. Such fertility restoring cotton stocks which are available from the University of Georgia have been identified by the Demeter I, Demeter II, and Demeter III designations. Also, Mississippi State University through the Delta Agricultural Experiment Station, Stoneville, Miss., is making available a cotton stock which possesses the requisite genetic system for fertility restoration under the DES 146C designation. Alternatively, the requisite genetic system for fertility restoration may be obtained from a commercially available $F_1$ hybrid cotton which was produced using such system such as the RA 3433H cotton hybrid. While using this source, subsequent generations of the cotton hybrid are grown out and selections are made for full fertility in the third and fourth generations to identify plants which are homozygous dominant for fertility restoration (i.e., plants which possess RfRf and EE gene pairs).

Once the requisite dominant genetic system for fertility restoration is confirmed, it may be added by crossing to standard narrow-leafed cotton stocks (e.g., the Pronto, Gumbo, etc., varieties). Also, a good source for cotton stocks possessing a narrow-leafed configuration (e.g., an okra-leafed configuration) is Louisiana State University (Baton Rouge, La.).

Seeds capable of forming narrow-leafed male fertile cotton plants for use in the process of the present invention when the broad-leafed male sterile plants are Tamcot A-788 or RA-A30 have been designated No. RA-R511-80-1 and have been deposited in the National Seed Storage Laboratory at Fort Collins, Colo., under Laboratory Accession No. GH-2374 Ser. No. 190,935. Such male parent stock was derived through selection from Demeter II which was obtained from the University of Georgia. Numerous other narrow-leafed male fertile cotton plant lines could be similarly derived and selected for use in the process of the present invention.

When carrying out the improved process for the efficient production of seeds capable of growing $F_1$ hybrid cotton plants in accordance with the present invention, the requisite parent plants heretofore described can be grown as either (1) a substantially random cotton plant population, or (2) as substantially uniform cotton plant populations of each parent which are grown in pollinating proximity to each other. The seeds required to produce the parent plants can be planted and cultivated in accordance with conventional cotton-growing procedures. For instance, the cotton seeds may be planted at a density of approximately 4 to 6 seeds per foot in rows having a width of approximately 32 to 40 inches. It is preferable that the parent plants be grown at an area which is isolated from other cotton plants so as to minimize the occurrence of outcrossing pollination from an unwanted source.

In a preferred embodiment of the process of the present invention, the cottonseed lots capable of producing the two parents are blended to form a substantially uniform random mixture prior to planting. An adequate number of the narrow-leafed male fertile plants are planted to provide ample pollen for the seed parent plants growing in the same area. The narrow-leafed male fertile plants commonly flower prolifically and hence are excellent pollen producers with good flower accessibility. They often can be provided in substantially lesser numbers than the female parent plants. For instance, the parent cottonseeds frequently can be blended prior to planting so that the resulting substantially random population of cotton plants comprises approximately 85 to 95 percent by a number of plants of the broad-leafed male sterile parent, and approximately 5 to 15 percent by number of plants of the narrow-leafed male fertile parent. In a particularly preferred embodiment of the process of the present invention, the substantially random population of cotton plants comprises approximately 90 to 95 percent by number of plants of the broad-leafed male sterile parent, and approximately 5 to 10 percent by number of plants of the narrow-leafed male fertile parent.

Alternatively, in another embodiment of the process of the present invention wherein substantially uniform populations of each parent are provided, the respective populations are grown sufficiently near to each other so that pollen can be transferred without loss of viability. For instance, the two types of parent cotton plants can be grown adjacent to each other as alternating strips. Such strips preferably take the configuration of adjoining rows which are planted with conventional cotton planting equipment. For instance, the substantially uniform population of broad-leafed male sterile cotton plants may consist of approximately 2 to 16 adjoining rows (e.g., 4 adjoining rows) which alternate with approximately 2 to 4 adjoining rows (e.g., 2 adjoining rows) of the narrow-leafed male fertile cotton plants.

Once the respective plants reach sufficient maturity to blossom, pollen is transferred from the narrow-leafed male fertile cotton plants to the broad-leafed male sterile cotton plants by any appropriate technique. The broad-leafed male sterile plants undergo cross-pollination and the narrow-leafed male fertile plants undergo self-pollination. In a preferred embodiment of the present process, the pollination is carried out with the aid of pollen-carrying insects that reliably visit the cotton blossoms. In a particularly preferred embodiment of the process, the pollination is carried out with the aid of honeybees. It has been found that more efficient cross-pollination can be carried out by a given quantity of bees if the respective parents are grown in rows in bulk as a substantially random population, since pollen-carrying insects such as honeybees have been found to demonstrate a greater propensity to travel along a given row of cotton plants than to travel from one row to another. During the pollination process of the present invention, it is recommended that the native bee population be augmented by hives of domesticated honeybees which are provided adjacent or within the planting area where the $F_1$ hybrid cottonseeds are produced. Such honeybee hives may be provided in a concentration of approximately 1 to 6 hives per acre. The beehives should, of course, be protected when spraying of the cotton-growing area with an insecticide takes place.

At the appropriate time in the life cycle of the cotton plants, the cottonseed product is harvested using conventional technology and the cottonseeds are recovered taking care to avoid contamination with cottonseeds from a foreign source. In an embodiment of the process in which both parents are grown as a substantially random population, the cottonseed product can be simply harvested from the entire planting area without any attempt to harvest separately the $F_1$ hybrid cottonseeds formed on the male sterile parents. Alternatively, in the embodiment of the process in which each parent is grown separately as a substantially uniform population, the cottonseed products formed on each parent are separately harvested taking care not to mix the same. In such instance the cottonseeds formed on the female parent plants are capable of forming male fertile $F_1$ hybrid cotton plants and the cottonseeds formed on male parent plants will form non-hybrid cotton plants. Such non-hybrid product can be disposed of appropriately.

Figure 3:
FIG. 3 shows a representative leaf configuration for an $F_1$ hybrid cotton plant which has resulted from the growing of the cottonseed formed in accordance with the process of the present invention. It will be noted that this leaf configuration is visually observable to be heterozygous and is intermediate in configuration between those of the parent plants illustrated in FIGS. 1 and 2.

Next, at least a portion of the cottonseeds obtained from the area where the male sterile plants were grown are planted and the resulting plants are observed with respect to leaf shape configuration. More specifically, a representative sample of such cottonseeds (e.g., a quantity preferably of at least one pound) is planted. When the cotton plants have developed to sufficient maturity to observe their leaf configurations, the number of cotton plants having a heterozygous leaf configuration which is intermediate to that of the leaf configurations of the parents is determined (preferably by visual observation) and is compared to the total number of plants from this cottonseed source. A typical heterozygous leaf configuration for a $F_1$ hybrid cotton plant derived from a male sterile broad-leafed parent pollinated by a male parent having an okra leaf configuration is illustrated in FIG. 3. Such plant would possess the gene pair $L°$ $l°$ with respect to leaf configuration. As will be apparent to those skilled in cotton plant leaf morphology, not all leaves present on a given cotton plant are likely to possess the exact number of lobes illustrated in FIG. 3. Regardless of the number of lobes present, the desired $F_1$ hybrid cotton plants will possess an observable intermediate leaf phenotype which may be readily distinguished from each parent.

Accordingly, the improved procedure for forming $F_1$ hybrid cottonseeds of the present invention is readily amenable to the determination and maintenance of a relatively high level of purity in the $F_1$ hybrid cottonseed product. In accordance with the concept of the present invention, frequently at least 75 percent of the cottonseeds recovered are capable of growing $F_1$ hybrid cotton plants on the basis of the determination previously described. Preferably, at least 90 percent of the cottonseeds recovered are capable of growing $F_1$ hybrid cotton plants, and most preferably, at least 95 percent of the cottonseeds recovered are capable of growing $F_1$ hybrid cotton plants on the basis of such determination. The determination of the relative purity of the $F_1$ hybrid cottonseed product is greatly simplified when compared to the laborious testing commonly required in the prior art. Thus, the seed producer can reliably ascertain the $F_1$ hybrid content of the seed to guide him in the accurate labeling and marketing of the seed. Also, the grower can be reliably informed in advance of the hybrid content of the planting seed he has purchased and can plan his agronomic practices accordingly.

While it is always the desire of seedsmen to maintain 100 percent purity in the foundation seed, this as a practical matter proves to be an elusive goal. In accordance with a preferred embodiment of the improved process of the present invention, the sources for the parental plants and/or the parental plants themselves, when grown as substantially uniform populations, are carefully monitored for the requisite leaf shape configurations. This may be done by visually observing the male sterile female parent line and its maintainer cotton plants and simply destroying any plants which fail to exhibit the required broad-leafed configuration. Also, one may visually observe the male fertile parent line and destroy any cotton plants which fail to exhibit the required narrow-leafed configuration. Any heterozygous leaf configurations which show up in either parent are recognized as an undesired outcross. Such an outcross may be destroyed by hand-roguing or by any other appropriate technique. The purity of the parent lines is accordingly enhanced as is the purity of the ultimate $F_1$ hybrid product which is produced therefrom. Without the process of the present invention it would have been necessary to detect unwanted male fertility or sterility by a tedious test-cross procedure involving much record keeping and the laborious tagging of large numbers of cotton plants. Accordingly, the process of the present invention overcomes significant disadvantages which have resided in the prior art and holds the promise of making hybrid cotton a reality to the farmer at a reasonable cost.

Hybrid cotton plants made possible by the process of the present invention were evaluated during 1983 in tests which were carried out by the Texas A & M University Agriculture Research and Extension Center at Lubbock, Tex. Data from these tests is reported in a memo publication entitled "Cotton Variety Tests in the Texas High Plains," 1983. One hybrid variety made possible by the process of the present invention was designated RAX-4507 and was found to yield 760 pounds of cotton lint per acre. Under the same growing conditions, a non-hybrid cotton variety known as Paymaster 404 which presently is widely grown on a commercial basis yielded 693 pounds of cotton lint per acre. Accordingly, an increase in yield of 67 pounds per acre was made possible with the resulting $F_1$ cotton hybrid during these tests.

Although the invention has been described with preferred embodiments, it is to be understood that variations and modifications may be resorted to, as will be apparent to those skilled in the art. Such variations and modifications are to be considered within the purview and scope of the claims appended hereto.

We claim:

1. An improved process for the efficient production of seeds capable of growing $F_1$ hybrid cotton plants comprising:

(a) growing in a planting area a substantially random population of (i) broad-leafed male sterile cotton plants wherein the broad leaf configuration is attributable to a recessive gene pair for such characteristic and said male sterility is attributable to the combination of an atypical Cms cytoplasm and a recessive genetic system for male sterility, and (ii) narrow-leafed male fertile cotton plants wherein the narrow leaf configuration is attributable to a partially dominant gene pair for such characteristic and said male fertility is attributable to a dominant genetic system for fertility restoration;

(b) pollinating said substantially random population of cotton plants whereby cottonseeds are formed on said male sterile cotton plants (i) which are capable of growing male fertile $F_1$ hybrid cotton plants which possess a visually observable heterozygous leaf configuration that is intermediate in configuration between the leaf configurations of parent plants (i) and (ii), and cottonseeds are formed on said narrow-leafed male fertile cotton plants (ii) which are capable of growing narrow-leafed non-hybrid cotton plants;

(c) recovering cottonseeds which have formed on said substantially random population of cotton plants in said planting area;

(d) growing at least a portion of the cottonseeds recovered in step (c); and (e) determining the approximate proportion of $F_1$ hybrid cottonseeds present in said cottonseeds recovered in said step (c) on the basis of the respective leaf shapes of said plants grown in step (d).

2. An improved process for the efficient production of seeds capable of growing $F_1$ hybrid cotton plants according to claim 1 wherein said substantially random population of cotton plants (i) and (ii) which is grown in step (a) is planted within rows.

3. An improved process for the efficient production of seeds capable of growing $F_1$ hybrid cotton plants according to claim 1 wherein said substantially random population of cotton plants (i) and (ii) which is grown in said planting area in step (a) comprises approximately 85 to 95 percent of (i) plants and approximately 5 to 15 percent of (ii) plants, based upon tne total number of cotton plants growing in said planting area.

4. An improved process for the efficient production of seeds capable of growing $F_1$ hybrid cotton plants according to claim 1 wherein said substantially random population of cotton plants (i) and (ii) which is grown in said planting area in step (a) comprises approximately 90 to 95 percent of (i) plants and approximately 5 to 10 percent of (ii) plants, based upon the total number of cotton plants growing in said planting area.

5. An improved process for the efficient production of seeds capable of growing $F_1$ hybrid cotton plants according to claim 1 wherein the broad leaf configuration of said male sterile cotton plants (i) is attributable to the recessive gene pair ll.

6. An improved process for the efficient production of seeds capable of growing $F_1$ hybrid cotton plants according to claim 1 wherein said narrow leaf configuration of said male fertile cotton plants (ii) is attributable to the partially dominant gene pair LL.

7. An improved process for the efficient production of seeds capable of growing $F_1$ hybrid cotton plants according to claim 1 wherein said narrow-leafed male fertile cotton plants (ii) possess a leaf configuration selected from the group consisting of okra, sub-okra, super-okra, laciniate, and mixtures of two or more of the foregoing.

8. An improved process for the efficient production of seeds capable of growing $F_1$ hybrid cotton plants according to claim 1 wherein said narrow-leafed male fertile cotton plants (ii) possess an okra leaf configuration which is attributable to the partially dominant gene pair $L° L°$.

9. An improved process for the efficient production of seeds capable of growing $F_1$ hybrid cotton plants according to claim 1 wherein said pollination in step (b) is carried out with the aid of pollen-carrying insects.

10. An improved process for the efficient production of seeds capable of growing $F_1$ hybrid cotton plants according to claim 1 wherein said pollination in step (b) is carried out with the aid of honeybees.

11. An improved process for the efficient production of seeds capable of growing $F_1$ hybrid cotton plants according to claim 1 wherein at least 75 percent of the cottonseeds recovered in step (c) are capable of growing $F_1$ hybrid cotton plants on the basis of the determination of step (e).

12. An improved process for the efficient production of seeds capable of growing $F_1$ hybrid cotton plants according to claim 1 wherein at least 90 percent of the cottonseeds recovered in step (c) are capable of growing $F_1$ hybrid cotton plants on the basis of the determination of step (e).

13. An improved process for the efficient production of seeds capable of growing $F_1$ hybrid cotton plants according to claim 1 wherein at least 95 percent of the cottonseeds recovered in step (c) are capable of growing $F_1$ hybrid cotton plants on the basis of the determination of step (e).

14. An improved process for the efficient production of seeds capable of growlng $F_1$ hybrid cotton plants according to claim 1 wherein the parental plants for cotton plants (i) and (ii), as well as the maintainer plants for plants (i), were grown as substantially uniform plant populations, the respective leaf configurations in each such population were visually observed, and plants growing in such substantially uniform plant populations having a non-conforming leaf configuration were substantially destroyed so as to enhance the purity of the parental lines.

15. An improved process for the efficient production of seeds capable of growing $F_1$ hybrid cotton plants comprising:

(a) growing a substantially uniform first population of broad-leafed male sterile cotton plants wherein the broad leaf configuration is attributable to a recessive gene pair for such characteristic and said male sterility is attributable to a combination of an atypical Cms cytoplasm and a recessive genetic system for male sterility in pollinating proximity to a substantially uniform second population of narrow-leafed male fertile cotton plants wherein the narrow leaf configuration is attributable to a partially dominant gene pair for such characteristic and said male fertility is attributable to a dominant genetic system for fertility restoration;

(b) pollinating said broad-leafed male sterile cotton plants of said first population with pollen from said narrow-leafed male fertile cotton plants of said second population whereby cottonseeds are formed on said broad-leafed male sterile cotton plants of said first population which are capable of growing male fertile $F_1$ hybrid cotton plants which possess a visually observable heterozygous leaf configuration that is intermediate in configuration between the leaf configurations of the bulk of the plants of said first and second populations;

(c) recovering the cottonseeds which have formed on said plants of said first population;

(d) growing at least a portion of the cottonseeds recovered in step (c); and (e) determining the approximate proportion of $F_1$ hybrid cottonseeds present in said cottonseeds recovered in said step (c) on the basis of the respective leaf shapes of the plants grown in step (d).

16. An improved process for the efficient production of seeds capable of growing $F_1$ hybrid cotton plants according to claim 15 wherein the substantially uniform populations of cotton plants of the first and second populations are grown within rows in step (a).

17. An improved process for the efficient production of seeds capable of growing $F_1$ hybrid cotton plants according to claim 15 wherein said first population of broad-leafed cotton plants consists of approximately 2 to 16 adjoining rows and alternates with approximately 2 to 4 adjoining rows of said narrow-leafed male fertile cotton plants of said second population in step (a).

18. An improved process for the efficient production of seeds capable of growing $F_1$ hybrid cotton plants according to claim 15 wherein said first population of broad-leafed male sterile cotton plants consists of approximately 4 adjoining rows and alternates with approximately 2 adjoining rows of said narrow-leafed male fertile cotton plants of said second population in step (a).

19. An improved process for the efficient production of seeds capable of growing $F_1$ hybrid cotton plants according to claim 15 wherein the broad leaf configuration of said male sterile cotton plants of said first population is attributable to the recessive gene pair ll.

20. An improved process for the efficient production of seeds capable of growing $F_1$ hybrid cotton plants according to claim 15 wherein said narrow leaf configuration of said male fertile cotton plants of said second population is attributable to the partially dominant gene pair LL.

21. An improved process for the efficient production of seeds capable of growing $F_1$ hybrid cotton plants according to claim 15 wherein said narrow-leafed male fertile cotton plants of said second population possess a leaf configuration selected from the group consisting of okra, sub-okra, super-okra, laciniate, and mixtures of two or more of the foregoing.

22. An improved process for the efficient production of seeds capable of growing $F_1$ hybrid cotton plants according to claim 15 wherein said narrow-leafed male fertile cotton plants of said second population possess an okra leaf configuration which is attributable to the partially dominant gene pair $L^° L^°$.

23. An improved process for the efficient production of seeds capable of growing $F_1$ hybrid cotton plants according to claim 15 wherein said crossing of step (b) is carried out with the aid of pollen-carrying insects.

24. An improved process for the efficient production of seeds capable of growing $F_1$ hybrid cotton plants according to claim 15 wherein said crossing in step (b) is carried out with the aid of honeybees.

25. An improved process for the efficient production of seeds capable of growing $F_1$ hybrid cotton plants according to claim 15 wherein at least 75 percent of the cottonseeds recovered in step (c) are capable of growing $F_1$ hybrid cotton plants on the basis of the determination of step (e).

26. An improved process for the efficient production of seeds capable of growing $F_1$ hybrid cotton plants according to claim 15 wherein at least 90 percent of the cottonseeds recovered in step (c) are capable of growing $F_1$ hybrid cotton plants on the basis of the determination of step (e).

27. An improved process for the efficient production of seeds capable of growing $F_1$ hybrid cotton plants according to claim 15 wherein at least 95 percent of the cottonseeds recovered in step (c) are capable of growing $F_1$ hybrid cotton plants on the basis of the determination of step (e).

28. An improved process for the efficient production of seeds capable of growing $F_1$ hybrid cotton plants according to claim 15 wherein the substantially uniform first and second populations of cotton plants were visually observed prior to step (b), and plants present therein having a nonconforming leaf configuration were substantially destroyed so as to enhance the purity of the respective plant populations prior to crossing in step (b).

* * * * *